(12) United States Patent
Wlassics et al.

(10) Patent No.: US 7,622,616 B2
(45) Date of Patent: *Nov. 24, 2009

(54) DEHALOGENATION PROCESS

(75) Inventors: Ivan Wlassics, Genoa (IT); Vito Tortelli, Milan (IT)

(73) Assignee: Solvay Solexis S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/417,159

(22) Filed: May 4, 2006

(65) Prior Publication Data

US 2006/0252968 A1  Nov. 9, 2006

(30) Foreign Application Priority Data

May 5, 2005  (IT)  ............................ MI2005A0817

(51) Int. Cl.
*C07C 41/24* (2006.01)
*C07D 317/10* (2006.01)

(52) U.S. Cl. .................. 568/657; 568/673; 568/674; 549/430; 549/455; 585/612

(58) Field of Classification Search .................. None
See application file for complete search history.

(56) References Cited

U.S. PATENT DOCUMENTS

| | | | |
|---|---|---|---|
| 3,242,218 A | 3/1966 | Sianesi et al. | |
| 3,715,378 A | 2/1973 | Resnick et al. | |
| 3,810,874 A | 5/1974 | Mitsch et al. | |
| 4,523,039 A | 6/1985 | Lagow et al. | |
| 4,647,413 A | 3/1987 | Savu | |
| 5,149,842 A | 9/1992 | Sianesi et al. | |
| 5,225,576 A | 7/1993 | Navarrini et al. | |
| 5,258,110 A | 11/1993 | Sianesi et al. | |
| 5,449,825 A | 9/1995 | Ishibe et al. | |
| 5,495,028 A | 2/1996 | Navarrini et al. | |
| 2001/0051753 A1* | 12/2001 | Navarrini | 568/615 |
| 2006/0252966 A1* | 11/2006 | Wlassics et al. | 568/24 |

FOREIGN PATENT DOCUMENTS

| | | |
|---|---|---|
| EP | 0 148 482 A2 | 7/1985 |
| EP | 0 239 123 A2 | 9/1987 |
| EP | 0 340 740 A2 | 11/1989 |
| EP | 0 633 257 A1 | 1/1995 |
| EP | 1 247 791 A1 | 10/2002 |
| EP | 1 333 020 A2 | 8/2003 |
| EP | 1 388 531 A1 | 2/2004 |
| EP | 1 454 940 A2 | 9/2004 |
| GB | 1 104 482 | 2/1968 |
| WO | WO 90/03357 | 4/1990 |

OTHER PUBLICATIONS

Navarrini W et al.; "New perfluorovinylethers through the bis(fluoroxy) difluoromethane (BDM)chemsitry"; Journal of Flourine Chemistry; vol. 125; No. 2, Feb. 2, 2004; pp. 189-197; XP004486522; ISSN: 0022-1139.

Houben-Weyl; Methods of Organic Chemistry; vol. E 10B2; 1999; Georg Thieme Verlag; Stuttgart; XP002441628; pp. 125-161.

Ameduri at al., "Synthesis and polymerization of fluorinated monomers bearing a reactive lateral group . . . ", J. Fluorine Chem., vol. 35, pp. 167-172, 1998.

Morken at el., "Preparation β, β-Difluoro-α-trifluoromethyl)styrenes by Palladium-Catalyzed Coupling of Aryl Iodides with Pentafluoropropen 2-ylzinc Reagent", J. Org. Chem., vol. 58, 1993, pp. 1167-1172.

* cited by examiner

*Primary Examiner*—Rosalynd Keys
(74) *Attorney, Agent, or Firm*—Arent Fox LLP

(57) ABSTRACT

A process for obtaining vinyl compounds by dehalogenation of halofluorinated compounds having a linear, branched or cyclic structure, said halofluorinated compounds containing in the molecule at least one group:

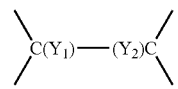

wherein $Y_1$ and $Y_2$, equal to or different from each other, are selected from Cl, Br, I;
wherein the halofluorinated compounds are dehalogenated in the presence of a transition metal, or of transition metal couples, by operating in a biphasic system of solvents immiscible among each other, formed of a (per)fluorinated solvent and a dipolar aprotic or protic solvent (co-solvent), wherein the ratio moles co-solvent/equivalents of the halofluorinated compound ranges from 0.5 to 10, preferably from 0.5 to 5, still more preferably from 1 to 3.

23 Claims, No Drawings

DEHALOGENATION PROCESS

The present invention relates to a process for obtaining fluorinated olefins by dehalogenation of halofluorinated compounds, containing in the molecule halogen atoms different from fluorine.

It is known in the prior art, see for example the Houben Weyl Encyclopedia, vol. E 10B2, pages 125-161, that the dehalogenation process of halofluorinated compounds, wherein the halogen is generally selected from chlorine and/or bromine, is carried out by using heterogeneous systems formed of one or more transition metals and of solvents which can be either hydrogenated protics, as alcohols, or hydrogenated ethers, as dioxane; or dipolar aprotics as DMF. The transition metal used is selected for example from zinc, manganese, copper. Metal couples as Zn/Cu, Zn/Sn, Zn/Hg can also be used. It is also known that, in dehalogenation reactions, saturated and/or unsaturated fluorinated reduction by-products containing hydrogen can be formed, thus lowering the yield of the main reaction product. According to the above reference, see in particular page 127, it is possible to increase the yields, and therefore to reduce the amount of undesired hydrogenated compounds, by using dipolar aprotic solvents. It is known in the prior art that, by using in the dehalogenation reactions dipolar aprotic solvents, as well as protic solvents, complexes are formed with the halogenated salt of the transition metal, the latter being produced during the reaction. For example, when zinc is used, the halogenated salt formed is the zinc chloride. From the industrial point of view the formation of the complex solvent-halogenated salt of the transition metal represents a drawback, as the recovery of the solvent becomes difficult. Furthermore, in the processes according to the prior art, it is important to avoid the prolonged contact between the dehalogenated reaction product and the solvent, since secondary reactions take place in the reaction raw product with consequent detriment of the yields.

One way to reduce some secondary reactions in the dehalogenation would be the removal, as quick as possible, of the dehalogenated compound formed in the reaction raw product. This can be carried out by distillation when the volatility of the dehalogenated product with respect to the solvent is high.

This is also valid for the purification of the obtained dehalogenated compound, which can contain hydrogenated byproducts having similar chemico-physical properties. Therefore the latter can hardly be separed from the main product. For applications wherein a high purity is required, as for example products for microlithography or monomers for polymeric optical fibers, it is important from an industrial point of view to obtain dehalogenated compounds having the highest possible purity degree. Therefore the presence of impurities hardly separable from the dehalogenated product represents a drawback from the industrial point of view.

The need was felt to have available a dehalogenation method of halofluorinated compounds containing chlorine and/or bromine, to obtain vinyl products having an improved yield combined with improved selectivity in comparison with the dehalogenation processes of the prior art and substantial decrease of hydrogenated by-products.

The Applicant has surprisingly and unexpectedly found a process to solve the above technical problem.

An object of the present invention is a process for obtaining vinyl compounds by dehalogenation of halofluorinated compounds having a linear, branched or cyclic structure, containing in the molecule at least one group:

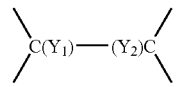

wherein $Y_1$ and $Y_2$, equal to or different from each other, are selected from Cl, Br, I;

characterized in that the halofluorinated compounds are dehalogenated in the presence of a transition metal, by operating in a biphasic system of solvents immiscible among each other, formed of a (per)fluorinated solvent and a dipolar aprotic solvent (co-solvent), wherein the ratio moles of cosolvent/equivalents of the halofluorinated compound ranges from 0.5 to 10, preferably from 0.5 to 5, still more preferably from 1 to 3.

As co-solvent, instead of a dipolar aprotic solvent, a protic solvent can be used.

With equivalents of the halofluorinated compound are meant the moles of halofluorinated compound multiplied by the number of groups

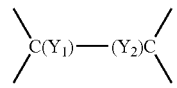

present in the compound.

The dehalogenation reaction can be applied to a wide range of halofluorinated products, provided that they do not contain functional groups capable to react with the transition metals, and with the (per)fluorinated solvent and the cosolvent forming the above described heterogeneous system.

According to the present invention, with solvents immiscible among each other it is meant that the solvents form two distinct phases.

Examples of classes of compounds to which the dehalogenation reaction can be applied are the following:

A) $T_1\text{-}(O)_{z''}\text{—}R_f\text{—}[(OCFY_1)_z\text{—}(CFY_1)_{z'}\text{—}CF_2Y_2]$ wherein:

$Y_1$ and $Y_2$ have the above meanings;

$z=0, 1$;

$z'=0, 1$, $z$ being different from $z'$;

$z''=0, 1$;

$R_f$ has the following meanings:

linear or branched $C_1\text{-}C_{20}$, preferably $C_1\text{-}C_{10}$, fluoroalkylene, preferably perfluoroalkylene, optionally containing one or more oxygen atoms;

(per)fluoropolyoxyalkylene, containing one or more of the following units statistically distributed along the chain:

$(C_3F_6O)$;

$(CFX_1O)$ wherein $X_1$ is F or $CF_3$;

$(C_2F_4O)$;

$(CF_2(CF_2)_{x'}CF_2O)$ wherein $x'$ is an integer equal to 1 or 2;

$(CR_4R_5CF_2CF_2O)$ wherein $R_4$ and $R_5$ are equal to or different from each other and are selected from H, Cl, and one fluorine atom of the perfluoromethylene unit can optionally be substituted with H, Cl or (per)fluoroalkyl, having for example from 1 to 4 carbon atoms;

when $R_f$ is (per)fluoroalkylene, $z''=0$ when za as defined below is 1; when $R_f$ is (per)fluoropolyoxyalkylene $z=0$, $z''=1$ when $za=0$;

$T_1$ is F or is a substituent having the following formula:

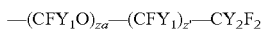
—(CFY$_1$O)$_{za}$—(CFY$_1$)$_{z'}$—CY$_2$F$_2$ wherein za is an integer equal to 0, 1; $Y_1$, $Y_2$, z' are as above;
B) dioxolanes of formula:

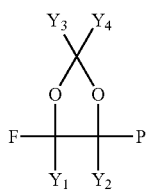

wherein:
$Y_1$ and $Y_2$ are as above;
P is F or $R_b$=$C_1$-$C_3$ perfluoroalkyl, $OR_b$;
$Y_3$ and $Y_4$, equal or different, are F, $CF_3$.

When in the compounds of formula A) $R_f$ is a (per)fluoropolyoxyalkylene substituent, it has number average molecular weight ranging from 66 to 12,000, preferably from 66 to 1,000, more preferably from 300 to 800.

When in the compounds of formula A) $R_f$ is a (per)fluoropolyoxyalkylene substituent the unit ($C_3F_6O$) of $R_f$ is selected from ($CF_2CF(CF_3)O$) or ($CF(CF_3)CF_2O$).

In the compounds of formula A) the perfluorooxyalkylene chains $R_f$ are selected, for example, from the following:

(a') —($CF_2CF_2O$)$_{p'}$($CF_2O$)$_{q'}$—
wherein:
p' and q' are integer numbers such that the q'/p' ratio is between 0.2 and 4, p' being different from zero, and the number average molecular weight is within the above range;

(b') —($CF_2CF(CF_3)O$)$_{r'}$—($CF_2CF_2O$)$_{s'}$—($CFX_1O$)$_{t'}$—
wherein:
$X_1$ is as above; r', s' and t' are integer numbers such that r'+s' is between 1 and 50, the t'/(r'+s') ratio is between 0.01 and 0.05, (r'+s') being different from zero, and the number average molecular weight is within the above range;

(c') —($CF(CF_3)CF_2O$)$_{u'}$—R'$_f$O—($CF(CF_3)CF_2O$)$_{u'}$—
wherein:
R'$_f$ is a $C_1$-$C_3$ bifunctional perfluoroalkyl radical; u' is an integer number such that the number average molecular weight is in the above range;

(c") ($CFX_1O$)$_{r'}$—($CF_2CF(CF_3)O$)$_{r'}$—R'$_f$O—($CF_2CF(CF_3)O$)$_{r'}$—($CFX_1O$)$_{t'}$—
wherein:
R'$_f$ is a $C_1$-$C_3$ bifunctional perfluoroalkyl radical; r', t' and $X_1$ are as above; r' and t' such that the number average molecular weight is in the above range;

(d') —($CF_2(CF_2)_xCF_2O$)$_{v'}$—
wherein:
v' is an integer number such that the number average molecular weight is comprised in the above range, x' is an integer equal to 1 or 2;

(e') —($CF_2CF_2CH_2O$)$_{w'}$—R'$_f$O—($CH_2CF_2CF_2O$)$_{w'}$—
wherein:
R'$_f$ is as above; w' is an integer number such that the number average molecular weight is in the above range. Preferably $R_f$ has structure (a') or (b').

By using the process of the invention, from the compounds of formula A) the respective compounds of vinylether and olefinic type are obtained; from the compounds of formula B) the corresponding dioxoles are obtained.

The compounds of formula A) containing as end unit —(OCFY$_1$)$_{za}$(CFY$_1$)$_{z'}$—CF$_2$Y$_2$, wherein $R_f$ is perfluoroalkyl and $T_1$ has the above meanings, when za=1 are obtainable with the process described in EP 1,388,531; EP 1,333,020, when za=0 are obtainable as described in the Houben Weyl Encyclopedia, vol. E 10B2, pages 125-161.

The compounds of formula A) containing as end unit —(OCFY$_1$)$_{za}$—(CFY$_1$)$_{z'}$—CF$_2$Y$_2$, $T_1$ as above and wherein $R_f$ is (per)fluoropolyoxyalkylene, can be prepared by starting from the corresponding (per)fluoropolyoxyalkylenes having —COF end groups. See for example patents GB 1,104,482, U.S. Pat. No. 3,715,378, U.S. Pat. No. 3,242,218, U.S. Pat. No. 4,647,413, EP 148,482, U.S. Pat. No. 4,523,039, EP 340,740, WO 90/03357, U.S. Pat. No. 3,810,874, EP 239,123, U.S. Pat. Nos. 5,149,842, 5,258,110.

The compounds of formula B) are obtainable with the process described in U.S. Pat. Nos. 5,225,576 and 5,495,028.

In the process of the present invention one generally operates at temperatures between room temperature (20° C.) and 200° C., preferably between 50° C. and 150° C., with the proviso that the reaction temperature is lower than the boiling temperature of the (per)fluorinated solvent and of the co-solvent used.

Generally one operates under atmospheric pressure.

The transition metals usable in the process of the present invention are preferably selected from the following: zinc, manganese, copper. Alternatively transition metal couples as for example Zn/Cu, Zn/Sn, Zn/Hg, can also be used.

As (per)fluorinated solvents, in the process of the present invention liquid and inert compounds in the above temperature range can be used. Compounds or respective mixtures, selected from (per)fluorocarbons, (per)fluoroethers, (per)fluoropolyethers, perfluoroamines, hydrofluoroethers or hydropolyfluoroethers, respectively HFE® and H-Galden® can for example be used. In hydrofluoroethers and in hydropolyfluoroethers the end groups of the fluorinated molecule are —H (H-Galden®), —OCH$_3$, —OC$_2$H$_5$, —OC$_3$H$_7$ (HFE). The latter are products by Solvay Solexis and 3M respectively. Preferably H-Galden® is used. Generally (per)fluorinated solvents having a high boiling point are used so as to have solvents with a low vapour pressure and thus avoiding dragging phenomena during the reaction. For example Galden®HT-200, having boiling point of about 200° C., or Galden®LS-215, having boiling point of about 215° C. can be used.

The used co-solvent must be liquid and substantially inert under the reaction conditions. For example compounds selected from the following classes can be used: linear or branched $C_1$-$C_8$ alcohols; dipolar aprotic solvents as dimethylformamide, dimethylacetamide, dimethylsulphoxide, morpholine, acetonitrile; ethers as diglyme, tetraglyme, 1,4-dioxane or mixtures thereof.

The reaction is generally carried out under stirring, by adding the halofluorinated compound to a mixture, previously brought to the reaction temperature, formed of the (per)fluorinated solvent, co-solvent, the metal or transition metal couples.

Usually the conversion into dehalogenated product is substantially complete (100% of conversion). The reaction times are generally lower than 8 hours.

The transition metal is used so that the ratio moles of transition metal/equivalents of halofluorinated compound is between 1 and 5, preferably between 1 and 2.

Even though the process of the present invention can be carried out by using variable amounts of (per)fluorinated solvent, one preferably operates by using ratios by weight (per)fluorinated solvent: halofluorinated compound from 1:2 to 1:20, preferably from 1:2 to 1:5.

As said, with the process of the present invention dehalogenated compounds are obtained containing amounts of hydrogenated by-products rather lower than those obtained by dehalogenating the same halofluorinated compounds by using the processes of the prior art. Besides the yields are improved. See the Examples. Furthermore, in the process of the present invention the yield and the selectivity in the dehalogenated product remain high even when the reaction product formed remains in the reaction raw product and is not separated from the raw product by distillation during the reaction, owing to its low volatility.

The following Examples are for illustrative and not limitative purposes of the present invention.

EXAMPLES

Determination of the Purity of the Compound Obtained by Dehalogenation

The reaction products have been identified and quantified by quantitative $^{19}$F-NMR and $^{1}$H-NMR, quantitative gaschromatography and mass spectroscopy.

Example 1A (Comparative)

Preparation of the Compound of Formula $CF_3CF_2OCF_2OCF=CF_2$ (VIII) (MOVE 1) by Starting from the Compound 1,2-dichloro 3,5-dioxa perfluoroheptane of Formula $CF_3CF_2OCF_2OCFClCF_2Cl$ (II) by Dehalogenation (Dechlorination) by Using a Prior Art Process.

The dechlorination reaction was carried out as described in B. Ameduri et Al., J. Fluorine Chem. 35 (1999) 1557-1566 and in P. A. Morken et Al., J. Org. Chem. 58 (1993) 1167-1172.

35 grams of DMF, employed as solvent, and 0.074 moles of Zn are placed in a 3-necked flask equipped with a dropping bottle, Vigreux, thermometer and magnetic anchor. The mixture is heated at 80° C. for 20 minutes so as to activate Zn, then 0.049 moles of (II) are dropped, prepared (ratio moles Zn/compound (II) equal to 1.5) according to EP 1,454,940, at a rate of 0.6 moles/hour. It is allowed to react under magnetic stirring at 80C up to complete conversion of (II), i.e. for 60 minutes. The dechlorination product is collected in a vacuum test tube graduated at the milliliter tenth, directly connected to the Vigreux by means of a still, and immersed into a cold bath (−80° C.). The conversion is followed by analyzing the raw product at intervals during the reaction by $^{19}$F-NMR analysis and controlling the olefin (VIII) ml which is collected in the trap at −80° C.

It has been found that the main hydrofluorinated product is the following: $CF_3CF_2OCF_2OCF_2CF_2H$ (XI). The residual amount in ppm of this compound is reported in Table 1.

Example 1B (Comparative)

Preparation of the Compound perfluoro 2,2,4-trifluoro-5-trifluoromethoxy-1,3-dioxole of Formula:

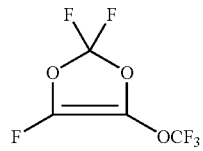

(IX)

starting from the compound perfluoro 2,2,4-trifluoro-4,5-dichloro-5-trifluoromethoxy-1,3-dioxole having formula:

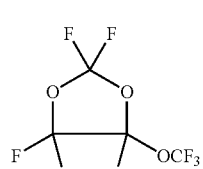

(III)

by dechlorination by using a prior art process.

The compound III is prepared acording to U.S. Pat. No. 5,495,028. The Example 1A (comparative) is repeated. It has been found that the main hydrofluorinated product is the following:

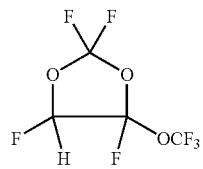

(XII)

The residual amount in ppm of this compound is reported in Table 1.

Example 1C (Comparative)

Preparation of the Compound perfluoro-1,3-butadiene of Formula $CF_2=CF-CF=CF_2$ (X) by Starting from the Compound perfluoro-1,2,3,4-tetrachloro-butane of Formula $CF_2Cl-CFCl-CFCl-CF_2Cl$ (VII) by Dechlorination by Using a Prior Art Process.

The Example 1A (comparative) is repeated. It has been found that the main hydrofluorinated product is the following: $HCF_2-CF=CF-CF_2H$ (XIII). The residual amount in ppm of this compound is reported in Table 1.

Example 2

Dehalogenation Procedure According to the Invention, Used in the Examples 2A-2C

An amount of HT-200® (perfluoropolyether Galden® Y having boiling point of 200° C.) equal to twice the weight of the halofluorinated compound, finely milled Zn in a molar amount equal to 1.5 times the moles of halofluorinated compound, and a molar amount of dimethylacetamide (DMA) (hydrogenated cosolvent) equal to twice the moles of halofluorinated compound are transferred into a 3-necked flask equipped with a dropping bottle, bubble condenser, thermometer and magnetic anchor. It is left under stirring at a temperature comprised between 80° C. and 110° C., specified in the Examples 2A-2C, and the halofluorinated compound is dropped at a rate of 0.6 eq/hour. It is left at the reaction temperature and under stirring until obtaining the complete conversion of the halofluorinated compound (about 2 hours). The conversion is followed by periodically analyzing the raw product by the above described analyses.

At the end of the reaction, the reaction raw product is filtered from the residual Zn and from the Zn salts formed during the conversion of the halofluorinated compound. The reaction product is removed from the fluorinated solvent and the hydrogenated co-solvent by distillation. The residual amount in ppm of the hydrofluorinated compound obtained in the Examples 2A-2C is reported in Table 1.

Example 2A

Dehalogenation (Dechlorination) Reaction of the Compound of Formula (II) $CF_3CF_2OCF_2OCFClCF_2Cl$ to Give the Compound (VIII) $CF_3CF_2OCF_2OCF=CF_2$ The process of the invention described in the Example 2 is utilized wherein the reaction temperature is 100° C. The obtained hydrofluorinated compound has formula $CF_3CF_2OCF_2OCF_2CF_2H$ (XI). The residual amount in ppm of the hydrofluorinated compound is reported in Table 1.

Example 2B

Dehalogenation (Dechlorination) Reaction of the Compound of Formula (III):

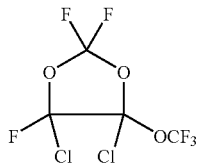

to give the compound (IX):

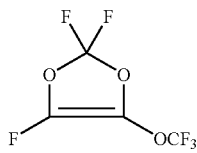

The process of the invention described in the Example 2 is utilized wherein the reaction temperature is 80° C. The residual amount in ppm of the hydrofluorinated compound of formula XII is reported in Table 1

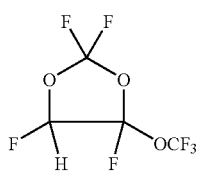

(XII)

Example 2C

Dehalogenation (Dechlorination) Reaction of the Compound of Formula (VII) $CF_2Cl—CFCl—CFCl—CF_2Cl$ to Give the Compound (X) $CF_2=CF—CF=CF_2$ The process of the invention described in the Example 2 is utilized wherein the reaction temperature is 110° C. The residual amount in ppm of the hydrofluorinated compound $HCF_2—CF=CF—CF_2H$ (XIII) is reported in Table 1.

Example 3

Dehalogenation Reaction by Using Diglyme as Co-Solvent

The Example 2A is repeated but by using as hydrogenated co-solvent the diglyme. The conversion of the compound of formula (II) is 20%; the selectivity in the compound (VIII) is 99.0%.

Example 4

Dehalogenation Reaction of the Compound $ClCF_2CFClO(CF_2)_4OCFClCF_2Cl$

The Example 2 is repeated but by using the above compound and the reaction temperature is 110° C. The products isolated from the reaction raw product are the following: $CF_2=CFO(CF_2)_4OCF=CF_2$ (XX) and $HCF_2CF_2O(CF_2)_4OCF_2CF_2H$ (XXI). The $^{19}F$-NMR (200 MHZ) analysis has shown that the amount of $—CF_2CF_2H$ end groups is 8,260 ppm on the total of the reaction mixture.

The selectivity in the $—OCF=CF_2$ and $—CF_2CF_2H$, end groups, respectively, is reported in Table 2.

Example 5 (Comparative)

Dehalogenation Reaction in DMF of the Compound $ClCF_2CFClO—(CF_2)_4OCFClCF_2Cl$ The Example 1 (comparative) is repeated, but by using the above compound and the reaction temperature is 110° C. It is found that in the reacted mixture, besides the main compound (XX), the compound (XXI) is present in an equal amount. The $^{19}F$-NMR (200 MHZ) analysis has shown that the amount of $—CF_2CF_2H$ end groups is 35,000 ppm (3.5% by weight) on the total of the reaction mixture.

The selectivity in the $—OCF=CF_2$ and $—CF_2CF_2H$ end groups, respectively, is reported in Table 2.

Comments to Table 2

Table 2 shows that, even when the obtained dehalogenated compound does not distil under the reaction conditions, the amount of hydrogenated by-products obtained with the process of the present invention is remarkably lower than that of the comparative Example.

TABLE 1

| Ex. 1A-1C Comp | Amount of hydrofluorinated compound expressed as ppm | |
|---|---|---|
| Ex. 2A-2C | Ex. 1 Comp | Ex. 2 |
| A | 900 | 230 |
| B | 800 | 150 |
| C | 650 | 100 |

TABLE 2

| Example | Selectivity | |
| --- | --- | --- |
| | —OCF=$CF_2$ end groups | —$CF_2CF_2H$ end groups |
| 4 | 99.2% | 0.826% |
| 5 Comparative | 96.5% | 3.5% |

The invention claimed is:

1. A process for obtaining perfluorovinyl compounds by dehalogenation of halofluorinated compounds having a linear, branched or cyclic structure, containing in the molecule at least one group:

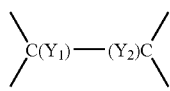

wherein $Y_1$ and $Y_2$, equal to or different from each other, are selected from Cl, Br, or I;
wherein the halofluorinated compounds are dehalogenated to remove chlorine, but not fluorine in the presence of a transition metal or a transition metal couple, by operating in a biphasic system of solvents immiscible among each other, formed of inert (per)fluorinated solvent and an aprotic dipolar or protic solvent (co-solvent), wherein the ratio moles of co-solvent/equivalents of the halofluorinated compound ranges from 0.5 to 10; wherein the halofluorinated compounds are selected from the following classes:

A) $T_1$—(O)$_{z''}$—$R_f$—[(OCF$Y_1$)$_z$—(CF$Y_1$)$_{z'}$—$CF_2Y_2$]
wherein:
$Y_1$ and $Y_2$ have the above meanings;
z=0 or 1;
z'=0 or 1, z being different from z';
z"=0 or 1;
$R_f$ has the following meanings:
linear or branched $C_1$-$C_{20}$ fluoroalkylene, optionally containing one or more oxygen atoms;
(per)fluoropolyoxyalkylene containing one or more of the following units statistically distributed along the chain:
($C_3F_6O$);
(CF$X_1$O) wherein $X_1$ is F or $CF_3$;
($C_2F_4O$);
(CF$_2$(CF$_2$)$_{x'}$CF$_2$O) wherein x' is an integer equal to 1 or 2;
(CR$_4$R$_5$CF$_2$CF$_2$O) wherein $R_4$ and $R_5$ are equal to or different from each other and are selected from H or Cl, and one fluorine atom of the perfluoromethylene unit is optionally substituted with H, Cl or (per)fluoroalkyl having from 1 to 4 carbon atoms;
when $R_f$ is (per)fluoroalkylene, z"=0 when za as defined below is 1;
when $R_f$ is (per)fluoropolyoxyalkylene z=0, z"=1 when za=0;
$T_1$ is F or is a substituent having the following formula:

$CF_2Y_2$—(CFY$_1$)$_{z'}$—(CFY$_1$O)$_{za}$— wherein za is an integer equal to 0 or 1; $Y_1$, $Y_2$, z' are as above;

B) dioxolanes of formula:

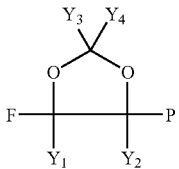

wherein:
$Y_1$ and $Y_2$ are as above;
P is F, $R_b$ wherein $R_b$ is $C_1$-$C_3$ perfluoroalkyl, or O$R_b$;
$Y_3$ and $Y_4$, equal or different, are F or $CF_3$.

2. A process according to claim 1, wherein, when in the compounds of formula A) $R_f$ is a (per)fluoropolyoxyalkylene substituent, it has number average molecular weight ranging from 66 to 12,000.

3. A process according to claim 1, wherein, when in the compounds of formula A) $R_f$ is a (per)fluoropolyoxyalkylene substituent, the unit ($C_3F_6O$) of $R_f$ is selected between ($CF_2CF(CF_3)O$) or ($CF(CF_3)CF_2O$).

4. A process according to claim 1, wherein in the compounds of formula A) the perfluorooxyalkylene chains $R_f$ are selected from:

(a') —($CF_2CF_2O$)$_{p'}$($CF_2O$)$_{q'}$—
wherein:
p' and q' are integer numbers such that the q'/p' ratio is between 0.2 and 4, p' being different from zero; and the number average molecular weight is between 66 and 12,000;

(b') —($CF_2CF(CF_3)O$)$_{r'}$—($CF_2CF_2O$)$_{s'}$—(CF$X_1$O)$_{t'}$—
wherein:
$X_1$ is as above; r', s' and t' are integer numbers such that r'+s' is between 1 and 50, the t'/(r'+s') ratio is between 0.01 and 0.05, (r'+s') being different from zero, and the number average molecular weight is between 66 and 12,000;

(c') —(CF($CF_3$)$CF_2O$)$_{u'}$R'$_f$O—(CF($CF_3$)$CF_2O$)$_{u'}$—
wherein:
R'$_f$ is a $C_1$-$C_3$ bifunctional perfluoroalkyl radical; u' is an integer number such that the number average molecular weight is between 66 and 12,000;

(c") (CF$X_1$O)$_{t'}$—(CF2CF($CF_3$)O)$_{r'}$—R'$_f$O—($CF_2$CF($CF_3$)O)$_{r'}$—(CF$X_1$O)$_{t'}$—
wherein:
R'$_f$ is a $C_1$-$C_3$ bifunctional perfluoroalkyl radical; r', t', and $X_1$ are as above; r' and t' such that the number average molecular weight is between 66 and 12,000:

(d') —(CF$_2$(CF$_2$)$_{x'}$CF$_2$O)$_{v'}$—
wherein:
v' is an integer number such that the number average molecular weight is between 66 and 12,000, x' is an integer equal to 1 or 2;

(e') —($CF_2CF_2CH_2O$)$_{w'}$—R'$_f$O—($CH_2CF_2CF_2O$)$_{w'}$—
wherein:
R'$_f$ is as above; w' is an integer number such that the number average molecular weight is between 66 and 12,000.

5. A process according to claim 4, wherein $R_f$ has structure (a') or (b').

6. A process according to claim 1, wherein the temperature is in the range 20° C.-200° C.

7. A process according to claim 1, wherein the transition metals are selected among zinc, manganese and copper.

8. A process according to claim 7, wherein transition metal couples are used.

9. A process according to claim 1, wherein the (per)fluorinated solvents are selected from (per)fluorocarbons, (per)fluoroethers, (per)fluoropolyethers, perfluoroamines, hydrofluoroethers, hydropolyfluoroethers or respective mixtures.

10. A process according to claim 1, wherein the co-solvent is selected from the following classes of compounds: linear or branched $C_1$-$C_8$ alcohols; dipolar aprotic solvents; ethers; or mixtures thereof.

11. A process according to claim 1, wherein the ratio moles of transition metal/equivalents of halofluorinated compound is between 1 and 5.

12. A process according to claim 1, wherein the ratio by weight (per)fluorinated solvent : halofluorinated compound ranges from 1:2 to 1:20.

13. A process according to claim 1, wherein the ratio moles of co-solvent/equivalents of the halofluorinated compound ranges from 0.5 to 5.

14. A process according to claim 1, wherein the ratio moles of co-solvent/equivalents of the halofluorinated compound ranges from 1 to 3.

15. A process according to claim 1, wherein $R_f$ is a linear or branched $C_1$-$C_{10}$ fluoroalkylene.

16. A process according to claim 1, wherein $R_f$ is a linear or branched $C_1$-$C_{20}$ perfluoroalkylene.

17. A process according to claim 3, wherein, $R_f$ is a (per)fluoropolyoxyalkylene substituent having a number average molecular weight ranging from 66 to 1,000.

18. A process according to claim 3, wherein, $R_f$ is a (per)fluoropolyoxyalkylene substituent having a number average molecular weight ranging from 300 to 800.

19. A process according to claim 7, wherein the temperature is in the range of 50° C.-150° C.

20. A process according to claim 8, wherein said transition metal couples are selected from the group consisting of Zn/Cu, Zn/Sn, and Zn/Hg.

21. A process according to claim 1, wherein the co-solvent is selected from the group consisting of: dimethylformamide, dimethylacetamide, dimethylsulphoxide, morpholine, acetonitrile, diglyme, tetraglyme, 1,4-dioxane, or mixtures thereof.

22. A process according to claim 1, wherein the ratio moles of transition metal/equivalents of halofluorinated compound is between 1 and 2.

23. A process according to claim 1, wherein the ratio by weight (per)fluorinated solvent:halofluorinated compound ranges from 1:2 to 1:5.

* * * * *